US009066874B2

(12) United States Patent
Deavenport et al.

(10) Patent No.: US 9,066,874 B2
(45) Date of Patent: Jun. 30, 2015

(54) DICATIONIC ETHERS WITH POLYHYDROXYL FUNCTIONALITY

(75) Inventors: Joseph L. Deavenport, Lake Jackson, TX (US); Nicole A. Brehm, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 80 days.

(21) Appl. No.: 14/007,094

(22) PCT Filed: Apr. 20, 2012

(86) PCT No.: PCT/US2012/034440
§ 371 (c)(1),
(2), (4) Date: Sep. 24, 2013

(87) PCT Pub. No.: WO2012/145620
PCT Pub. Date: Oct. 26, 2012

(65) Prior Publication Data
US 2014/0031590 A1    Jan. 30, 2014

Related U.S. Application Data

(60) Provisional application No. 61/477,880, filed on Apr. 21, 2011.

(51) Int. Cl.
| | |
|---|---|
| C07C 221/00 | (2006.01) |
| C07C 223/00 | (2006.01) |
| A61K 8/41 | (2006.01) |
| A61Q 5/12 | (2006.01) |
| C07C 217/08 | (2006.01) |
| A61Q 19/00 | (2006.01) |
| C07C 217/42 | (2006.01) |

(52) U.S. Cl.
CPC . *A61K 8/416* (2013.01); *A61Q 5/12* (2013.01); *C07C 217/08* (2013.01); *A61Q 19/00* (2013.01); *C07C 217/42* (2013.01)

(58) Field of Classification Search
CPC ............................ C07C 215/40; C07C 215/90
See application file for complete search history.

(56) References Cited

U.S. PATENT DOCUMENTS

| | | | |
|---|---|---|---|
| 4,597,962 | A | 7/1986 | Grollier et al. |
| 6,177,577 | B1 | 1/2001 | Roerden et al. |
| 6,869,977 | B1 | 3/2005 | O'Lenick et al. |
| 7,176,172 | B2 | 2/2007 | Harding et al. |
| 7,282,471 | B2 | 10/2007 | Harichian et al. |
| 7,541,496 | B2 | 6/2009 | Deavenport et al. |
| 2007/0048235 | A1 | 3/2007 | Harmalker et al. |

FOREIGN PATENT DOCUMENTS

| | | | |
|---|---|---|---|
| JP | 2002293002 | * | 10/2002 |
| WO | 2007025093 | A2 | 3/2007 |

OTHER PUBLICATIONS

Arch Personal Care Product Brochure—Honeyquat 50 Substantive Honey Derivative, Jan. 2004.
Colonial Chemical, Inc. Product Brochure—Cola® Moist 300P, 2007.
Colonial Chemical, Inc. Product Brochure—Cola® Moist 200, 2008.

* cited by examiner

*Primary Examiner* — Sudhakar Katakam
*Assistant Examiner* — Jennifer C Sawyer
(74) *Attorney, Agent, or Firm* — Edward L. Brant

(57) ABSTRACT

Described are novel dicationic polyhydroxyl compounds and their uses in personal care compositions.

17 Claims, No Drawings

DICATIONIC ETHERS WITH POLYHYDROXYL FUNCTIONALITY

CROSS REFERENCE TO RELATED APPLICATIONS

This application is a 35 USC §371 national phase filing of PCT/US2012/034440 filed Apr. 20, 2012, which claims the benefit of U.S. Application No. 61/477,880, filed Apr. 21, 2011.

FIELD

The present invention relates to novel dicationic polyhydroxyl compounds and their uses in personal care compositions.

BACKGROUND

Polyhydroxyl compounds, or polyols, have a number of uses, from raw materials used in the manufacture of urethane foams to humectants for personal care products like shaving foams, lotions, and shampoos.

Quaternary ammonium compounds are also useful in a number of applications, such as for disinfectants, surfactants, fabric softeners, and conditioners in shampoos.

Despite the number of available conventional compounds, there is a strong need for novel compounds with properties to differentiate performance or offer synergistic effects in areas of interest, particularly in personal care compositions.

DETAILED DESCRIPTION

In one embodiment, the present invention provides compounds, including salts, of the Formula (I):

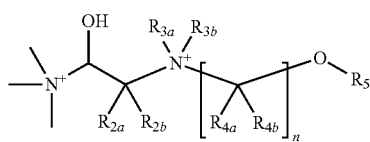

(I)

wherein:
wherein:
n is 1, 2, 3, 4, 5, or 6;
$R_{1a}$, $R_{1b}$, $R_{2a}$, $R_{2b}$, $R_{4a}$, and $R_{4b}$, are, independently at each occurrence, H or optionally substituted C1-C6 alkyl; and
$R_{3a}$, $R_{3b}$ and $R_5$ are, independently, optionally substituted C1-C6 alkyl.

The term "optionally substituted" as used herein means that the groups in question are either unsubstituted or substituted with one or more groups, radicals or moieties, selected from halogen, hydroxy, amino or carboxy. When the groups in question are substituted with more than one substituent, the substituents may be the same or different. In one embodiment, the optional substituent is selected to produce a cosmetically acceptable compound. "Cosmetically acceptable" refers to ingredients typically used in personal care compositions, and is intended to underscore that materials that are toxic, irritating, or unpleasant smelling when present in the amounts typically found in personal care compositions are not contemplated as part of the present invention. In one embodiment, the optional substituent is hydroxy.

"Alkyl" means a saturated monovalent linear or branched aliphatic hydrocarbon radical. Representative examples include, but are not limited to methyl, ethyl, propyl, isopropyl, butyl, isobutyl, tert-butyl, sec-butyl, pentyl, isopentyl, neopentyl, hexyl, isohexyl, and the like.

The term "cycloalkyl" denotes a saturated monocyclic or bicyclic cycloalkyl group. Examples of cycloalkyl groups include cyclopropyl, cyclobutyl, cyclopentyl, cyclohexyl, cycloheptyl, cyclooctyl, and the like. In one embodiment, the cycloalkyl is cyclohexyl or cyclopentyl.

Salts means that a counter-ion is present, preferably halogen, more preferably $Cl^-$.

In one embodiment, n is 2, 3, or 4. Preferably, n is 2.

In some embodiments, $R_{4a}$ and $R_{4b}$ are H at each occurrence. In some embodiments, at least one $R_{4a}$ is $-CH_3$, $-CH_2OH$, or $-CH_2CH_3$. Alternatively, $R_{4a}$ and $R_{4b}$ may cooperate, along with the carbon to which they are attached, to form a cycloalkyl group.

In one embodiment, $R_{1a}$ and $R_{1b}$ are each H.

In one embodiment, $R_{2a}$ and $R_{2b}$ are each H.

In some embodiments, $R_{3a}$ and $R_{3b}$ are the same. Examples of such embodiments include those where $R_{3a}$ and $R_{3b}$ are each $-CH_3$, those where $R_{3a}$ and $R_{3b}$ are each $-CH_2CH_3$, and those where $R_{3a}$ and $R_{3b}$ are each $-CH_2CH_2OH$.

Alternatively, in some embodiments, $R_{3a}$ and $R_{3b}$ are not the same. Examples of such embodiments include those where $R_{3a}$ is $-CH_2CH_2OH$. In one embodiment, $R_{3a}$ is $-CH_2CH_2OH$ and $R_{3b}$ is $-(CH_2)_3CH_3$.

In a preferred embodiment, $R_5$ is $-CH_2CH_2OH$.

Non-limiting examples of compounds of Formula I include the reaction products of 3-chloro-1,2-propanediol and amino ether alcohols. Non-limiting examples of these include 2-(2-dimethylamino)ethoxyethanol, 2-[2-(diethylamino)ethoxy]ethanol, ethyl(2-hydroxyethyl)[2-(2-hydroxyethoxy)ethyl]amine, and 2-[2-(dimethylamino)-1-methylethoxy]ethanol.

In one embodiment, the present invention provides methods for providing humectancy in a personal care composition, comprising including the compound of Formula I into the personal care composition. The ingredients used, and their proportions and manner of addition, are familiar to those versed in conventional personal care compositions, including, optionally, cosmetically acceptable emollients, moisturizers, conditioners, oils, sunscreens, surfactants, emulsifiers, preservatives, rheology modifiers, colorants, preservatives, pH adjustors, propellants, reducing agents, fragrances, foaming or de-foaming agents, tanning agents, depilatory agents, astringents, antiseptics, deodorants, antiperspirants, insect repellants, bleaches, tighteners, anti-dandruff agents, adhesives, polishes, strengtheners, fillers, barrier materials, or biocides.

In one embodiment, the present invention provides hair care compositions containing the compound of Formula I.

In one embodiment, the present invention provides skin care compositions containing the compound of Formula I.

EXAMPLES

The following examples are for illustrative purposes only and are not intended to limit the scope of the present invention.

Example 1

Reaction of 3-chloro-2-hydroxypropyltrimethylammonium chloride and 2-(2-dimethylamno)ethoxyethanol to afford 2-hydroxy-$N^1$-(2-(2-hydroxyethoxy)ethyl)-$N^1$, $N^1$,$N^3$, $N^3$, $N^3$-pentamethylpropane-1,3-diaminium chloride

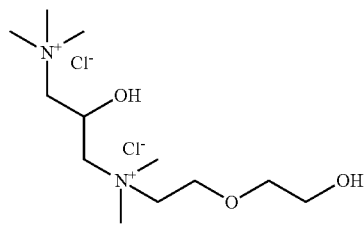 [SMILES: C[N+](C)(C)CC(O)C[N+](C)(C)CCOCCO ; [Cl-] ; [Cl-]]

A 500 mL round bottom, jacketed, flask was equipped with a magnetic stir bar and placed on a stir-plate. The temperature of the circulating bath was set to 10° C. and monitored with a thermocouple. 3-chloro-2-hydroxypropyltrimethylammonium chloride, available from The Dow Chemical Company under the trademark QUAT 188,100 g (50% solution; 0.27 mole) was added to the reactor flask. Next, about 23 g of NaOH solution (50% solution) was added over 30 minutes to increase the pH of the solution above 12. The circulation bath was held at 10° C. while 37.3 g (0.28 mol) of 2-(2-dimethylamino)ethoxyethanol was added dropwise over about 1 hour. Once all of the amine was added, the contents were reacted for 1 hour at 10° C. The temperature was then increased to 45° C. for 2.5 hours. The heat source was removed and the contents were then cooled to ambient temperature and the pH was adjusted to 7 using concentrated hydrochloric acid. The reaction solution was filtered through Whatman number 42 filter paper using a Buchner funnel and house vacuum.

$^{13}$C NMR spectra acquired from a Bruker 300 MHz spectrometer (samples prepared as ~30 wt % in $D_2O$) confirmed the title compound: DEPT NMR (250 MHz, D2O) (53.0, 53.2), 54.5, 60.4, 62.1, 64.2, 64.8, 66.6, 67.7, 72.0

Example 2

Reaction of 3-chloro-2-hydroxypropyltrimethylammonium chloride and 2-[2-(diethylamino)ethoxy]ethanol to afford $N^1$, $N^1$-diethyl-2-hydroxy-$N^1$-(2-(2-hydroxyethoxy)ethyl)-$N^3$, $N^3$, $N^3$-trimethylpropane-1,3-diaminium chloride

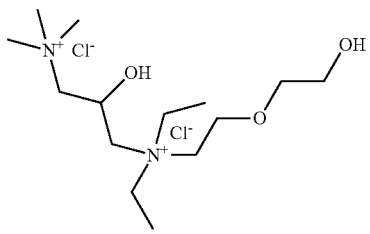 [SMILES: CC[N+](CC)(CCOCCO)CC(O)C[N+](C)(C)C ; [Cl-] ; [Cl-]]

The title compound is prepared substantially according to the protocol of Example 1, except that the conditions and amounts of reactants may vary, typically a 1:1 mol ratio with a slight excess of 3-chloro-2-hydroxypropyltrimethylammonium chloride, but which factors are well within the skill of one ordinarily skilled in the art.

Example 3

Reaction of 3-chloro-2-hydroxypropyltrimethylammonium chloride and Ethyl(2-hydroxyethyl)[2-(2-hydroxyethoxy)ethyl]amine to afford $N^1$-ethyl-2-hydroxy-$N^1$-(2-(2-hydroxyethoxy)ethyl)-$N^1$-(2-hydroxyethyl)-$N^3$, $N^3$, $N^3$-trimethylpropane-1,3-diaminium chloride

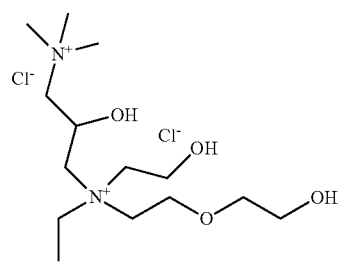 [SMILES: [Cl-] ; CC[N+](CCO)(CCOCCO)CC(O)C[N+](C)(C)C ; [Cl-]]

The title compound is prepared substantially according to the protocol of Example 1, except that the conditions and amounts of reactants may vary, typically a 1:1 mol ratio with a slight excess of 3-chloro-2-hydroxypropyltrimethylammonium chloride, but which factors are well within the skill of one ordinarily skilled in the art.

Example 4

Reaction of 3-chloro-2-hydroxypropyltrimethylammonium chloride and 2-[2-(Dimethylamino)-1-methylethoxy]ethanol to afford 2-hydroxy-$N^1$-(2-(2-hydroxyethoxy)propyl)-$N^1$, $N^1$, $N^3$, $N^3$, $N^3$-pentamethylpropane-1,3-diaminium chloride

The title compound is prepared substantially according to the protocol of Example 1, except that the conditions and amounts of reactants may vary, typically a 1:1 mol ratio with a slight excess of 3-chloro-2-hydroxypropyltrimethylammonium chloride, but which factors are well within the skill of one ordinarily skilled in the art.

Example 5

Compounds prepared substantially according to the Examples 1-4 are made and formulated into personal care compositions having otherwise conventional ingredients. The compositions are evaluated by trained panelists, with each panelist being asked to compare the inventive compositions to a conventional composition.

For hair care compositions, wet and dry feel preference and wet and dry combability is measured by asking the panelists to feel and comb two hair tresses of European virgin brown hair, commercially available from International Hair Importers and Products Inc. NY (USA), one hair tress treated with an inventive composition, the other hair tress treated with a conventional composition. Each panelist is asked to compare the tresses and state which tress is smoother to comb/feel. The answer "same" is not allowed. The reported number is the percent of panelists preferring one over the other.

For skin care compositions, panelists apply a sample (one inventive composition, one conventional composition) to a designated area on their right or left forearm. Initially, each sample is evaluated for ease of application, play time, evenness of deposit, coverage, speed of adsorbtion, shine, matte, skin moistness, heaviness, amount of grease, amount of tack, quickness of drying, overall skin feel, and overall appearance. After a designated time, each sample is again evaluated, this time for coverage, evenness of coverage, shine, matte, skin moistness, heaviness, and overall appearance.

It is understood that the present invention is not limited to the embodiments specifically disclosed and exemplified herein. Various modifications of the invention will be apparent to those skilled in the art. Such changes and modifications may be made without departing from the scope of the appended claims. Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A compound, or salts thereof, of Formula (I):

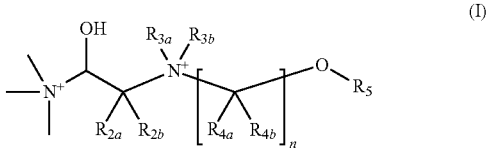

(I)

wherein:
n is 1, 2, 3, 4, 5, or 6;
$R_{2a}$, $R_{2b}$, $R_{4a}$, and $R_{4b}$, are, independently at each occurrence, H or optionally substituted C1-C6 alkyl; and
$R_{3a}$, $R_{3b}$ and $R_5$ are, independently, optionally substituted C1-C6 alkyl, with the proviso that $R_5$ is not substituted with an epoxide.

2. The compound of claim 1, wherein n is 2, 3, or 4.

3. The compound of claim 1, wherein $R_{2a}$ and $R_{2b}$ are each H.

4. The compound of claim 1, wherein $R_{3a}$ and $R_{3b}$ are the same.

5. The compound of claim 4, wherein $R_{3a}$ and $R_{3b}$ are each —$CH_3$.

6. The compound of claim 4, wherein $R_{3a}$ and $R_{3b}$ are each —$CH_2CH_3$.

7. The compound of claim 4, wherein $R_{3a}$ and $R_{3b}$ are each —$CH_2CH_2OH$.

8. The compound of claim 1, wherein $R_{3a}$ and $R_{3b}$ are not the same.

9. The compound of claim 8, wherein $R_{3a}$ is —$CH_2CH_2OH$.

10. The compound of claim 9, wherein $R_{3b}$ is —$(CH_2)_3CH_3$.

11. The compound of claim 1, wherein at least one $R_{4a}$ is $CH_3$.

12. The compound of claim 1, wherein $R_{4a}$ is —$CH_2OH$.

13. The compound of claim 1, wherein $R_{4b}$ is —$CH_2CH_3$.

14. The compound of claim 1, wherein $R_{4a}$ and $R_{4b}$ cooperate to form a cyclohexyl group.

15. The compound of claim 1, wherein $R_5$ is —$CH_2CH_2OH$.

16. A hair care composition containing the compound of claim 1.

17. A skin care composition containing the compound of claim 1.

* * * * *